United States Patent
Youn et al.

(10) Patent No.: US 6,846,931 B2
(45) Date of Patent: Jan. 25, 2005

(54) ORGANIC ACID SALT OF AMLODIPINE

(75) Inventors: Yong Sik Youn, Yongin-si (KR); Seong Hwan Cho, Suwon-si (KR); Choong Sil Park, Icheon-si (KR); Yun Cheul Kim, Seoul (KR); Dong Kwon Lim, Seongnam-si (KR); Sung Hak Jung, Seoul (KR); Sung Hak Lee, Yongin-si (KR); Hyun Suk Kang, Seoul (KR); Kyung Mi Park, Seoul (KR); Yun Taek Jung, Seoul (KR); Young Hoon Kim, Seoul (KR); Kyu Jeong Yeon, Yongin-si (KR); Myeong Yun Chae, Seongnami-si (KR); Hae Tak Jin, Yongin-si (KR); Hea Ran Suh, Ichon-si (KR); Kwang Hyeg Lee, Seongnam-si (KR); Hyuk Koo Lee, Yongin-si (KR)

(73) Assignee: CJ Corp, Seoul (KR)

( * ) Notice: Subject to any disclaimer, the term of this patent is extended or adjusted under 35 U.S.C. 154(b) by 0 days.

(21) Appl. No.: 10/642,754

(22) Filed: Aug. 19, 2003

(65) Prior Publication Data

US 2004/0158075 A1 Aug. 12, 2004

(30) Foreign Application Priority Data

Aug. 21, 2002 (KR) .............................. 10-2002-0049422

(51) Int. Cl.[7] ............................................. C07D 211/86
(52) U.S. Cl. ....................................................... 546/321
(58) Field of Search ........................................... 546/321

(56) References Cited

U.S. PATENT DOCUMENTS

| | | |
|---|---|---|
| 4,572,909 A | 2/1986 | Campbell et al. |
| 4,758,569 A | 7/1988 | Swindell |
| 4,806,557 A | 2/1989 | Campbell et al. |
| 4,879,303 A | 11/1989 | Davison et al. |
| 6,057,344 A | 5/2000 | Young |
| 6,291,490 B1 | 9/2001 | Young |
| 6,756,390 B2 | 6/2004 | Cho et al. |
| 2002/0086888 A1 | 7/2002 | Benneker et al. |

FOREIGN PATENT DOCUMENTS

| | | |
|---|---|---|
| EP | 0089167 | 9/1983 |
| EP | 0244944 | 3/1987 |
| KR | 95-7228 | 4/1989 |
| KR | 19912145 | 4/1989 |
| KR | 20076561 | 10/2002 |
| WO | 99/52873 | 10/1999 |
| WO | 02053538 | 7/2002 |

OTHER PUBLICATIONS

English Language abstract of Korean Application No. 1020020076561. dated Oct. 11, 2002.

*Primary Examiner*—Patricia L. Morris
(74) *Attorney, Agent, or Firm*—Greenblum & Bernstein, P.L.C.

(57) ABSTRACT

Disclosed are a novel organic acid salt of amlodipine, its preparation method, and a pharmaceutical composition containing the same as a therapeutically active ingredient.

4 Claims, No Drawings

ORGANIC ACID SALT OF AMLODIPINE

BACKGROUND OF THE INVENTION

1. Field of the Invention

The present invention relates to a novel organic acid salt of amlodipine (2-[(2-aminoethoxy)methyl]-4-(2-chlorophenyl)- 1, 4-dihydro-6-methyl-3,5-pyridinedicarboxylic acid 3-ethyl 5-methyl ester), represented by the following chemical formula 1, its preparation method, and a pharmaceutical composition containing the same as an effective ingredient.

[Chemical Formula 1]

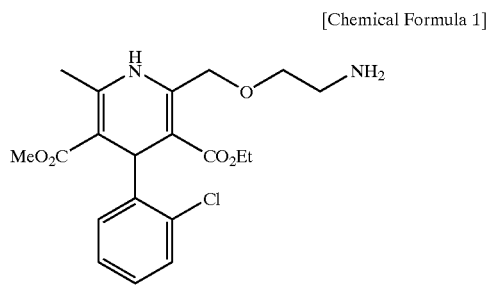

2. Description of the Prior Art

With activity to block calcium channels in the body, amlodipine is used for the treatment of hypertension. This calcium channel blocker is found in many prior arts.

European Pat. Laid-Open Publication No. 89,167 discloses acid salts of amlodipine which can be formed from acids which may form nontoxic acid addition salts with pharmaceutically acceptable anions, such as hydrochloride, hydrobromide, sulfate, phosphate, acetate, maleate, fumarate, lactate, tartrate, citrate, gluconate, etc.

U. S. Pat. No. 6,291,490 introduces a pharmaceutical composition containing as an active ingredient S-(-)-amlodipine which possesses potent activity in treating hypertension without the adverse effects associated with the administration of the racemic mixture of amlodipine.

Both U.S. Pat. No. 4,879,303 and Korean Pat. Laid-Open Publication No. 1989-3375 disclose amlodipine besylate, saying that amlodipine besylate is superior to other salts of amlodipine, such as hydrochloride, acetate and mesylate in physicochemical properties including (1) solubility, (2) stability, (3) non-hygroscopicity, and (4) processability for tablet formulation.

However, since amlodipine besylate in current use is relatively low in solubility at pH 1–7.4, there is a need for novel salts which are of sufficient solubility, so as to increase the bioavailability of amlodipine and easily formulate its injections. Additionally, amlodipine besylate is found to be sensitive to light, so that decompositon products are observed.

Further, amlodipine besylate is disadvantageous due to benzene sulfonic acid being used in its production process. That is, benzene sulfonic acid is difficult to industrially treat because it is corrosive and toxic. In addition, its high hygroscopicity requires special procedures for its transport, delivery and use. Another disadvantage is that the water content of benzene sulfonic is too high, amounting to about 10%. In order to avoid these problems, ammonium benzene sulfonate is employed as an alternative, but with concomitant generation of ammonia gas. This method needs additional processes for absorbing and inactivating ammonia gas (PCT Publication No. WO1999/52873).

DISCLOSURE OF THE INVENTION

Leading to the present invention, the intensive and thorough research into therapeutically effective organic acid salts of amlodipine, conducted by the present inventors aiming to overcome the problems encountered in prior arts, resulted in the finding that amlodipine pyroglutamate has excellent physicochemical properties including solubility, non-hygroscopicity, chemical and light stability, and processability for dosage formation, as well as the fact that pyroglutamic acid is less toxic and corrosive than benzene sulfonic acid, so that the amlodipine pyroglutamate is industrially and medically useful.

Therefore, it is an object of the present invention to provide a pyroglutamic acid salt of amlodipine.

It is another object of the present invention to provide a method for preparing a pyroglutamic acid salt of amlodipine.

It is a further object of the present invention to provide a pharmaceutical composition containing the pyroglutamic acid salt of amlodipine as a therapeutically active ingredient.

In accordance with an aspect of the present invention, there is provided a pyroglutamic acid salt of amlodipine, preferably amlodipine (S)-(-)-pyroglutamate or amlodipine (R)-(+)-pyroglutamate, and more preferably a crystalline pyroglutamic acid salt of amlodipine.

In accordance with another aspect of the present invention, there is provided a method for preparing a pyroglutamate acid salt of amlodipine, in which (S)-(-)-pyroglutamic acid or (R)-(+)-pyroglutamic acid is reacted with amlodipine in an inert solvent.

In accordance with a further aspect of the present invention, there is provided a pharmaceutical composition effective in treating ischemic cardiac disorders or hypertension, comprising a therapeutically effective amount of amlodipine pyroglutamate and a pharmaceutically acceptable diluent or carrier preferably in the dosage form of tablets, capsules, solutions or injectables.

DETAILED DESCRIPTION OF THE INVENTION

The present invention encompasses amlodipine pyroglutamate, represented by the following chemical formula 2.

[Chemical Formula 2]

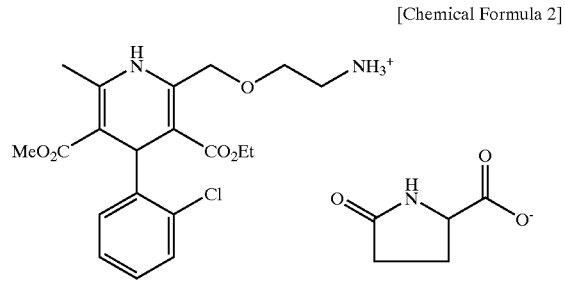

Compared to amlodipine besylate in a commercially acceptable form, amlodipine pyroglutamate exhibits equal or better non-hygroscopicity, formulation processability and chemical stability and especially, at least 200 times greater solubility in distilled water or under various pH conditions. Accordingly, with the feasibility of being formulated into solutions and injectables as well as the difficulty of being precipitated in blood, the amlodipine pyroglutamate of the present invention is of great bioavailability. An extraordinary improvement in stability to light is found in the pyroglutamate over other known organic acid salts, so that it can be stably stored for a long period of time without losing its medicinal effect as an anti-hypertensive agent.

Pyroglutamic acid suitable for the preparation of the amlodipine pyroglutamate of the present invention may be a racemic mixture or an optically pure material with preference to an optically pure material, that is, (S)-(−)-pyroglutamic acid or (R)-(+)-pyroglutamic acid.

Pyroglutamic acid salts of amlodipine according to the present invention may be in a crystal form or an amorphous form with preference to a crystal form.

The present invention also encompasses a method for preparing pyroglutamic acid salts of amlodipine. The salts can be prepared by reacting amlodipine with pyroglutamic acid in an inert solvent, as seen in the following reaction formula 1.

[Reaction Formula 1]

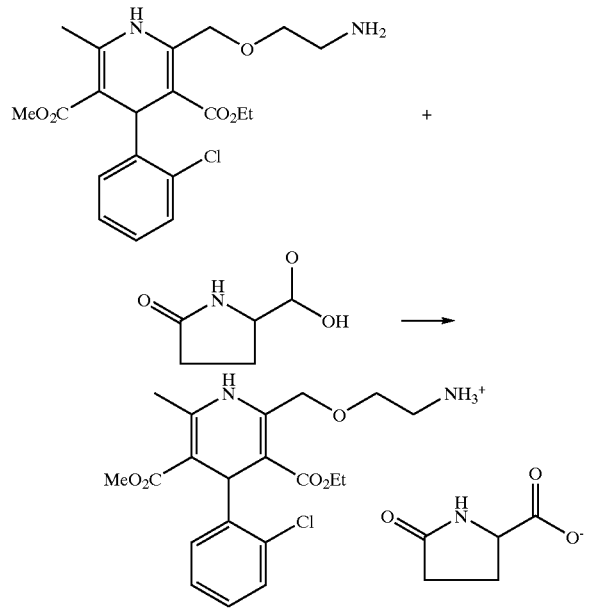

Pyroglutamic acid (also called 2-oxo-pyrrolidone carboxylic acid, or PCA) used in the method according to the present invention is a non-toxic amino acid naturally occurring in vegetables, fruits, dairy products, and meat as white solid. Other names for pyroglutamate include pidolic acid, glutimic acid, glutiminic acid, glutamic acid lactam, 5-oxo-2-pyrrolidin carboxylic acid, 5-oxo proline, 2-pyrrolidone-5-carboxylic acid, alpha-aminoglutaric acid lactam. It is also normally present in large amounts in the human brain, cerebrospinal fluid, and blood. Pyroglutamate is known to have a number of remarkable effects of improving cognitive functions of the brain. After oral administration, pyroglutamate passes into the brain through the blood-brain barrier and stimulates cognitive functions. Pyroglutamate improves memory and learning in rats.

In addition, because it is easy to handle industrially as well as being inexpensive, pyroglutamic acid is produced on a mass scale.

Examples of the inert solvent suitable for the preparation of the salts of present invention include ethyl acetate, methanol, ethanol, isopropanol, acetonitrile, hexane, isopropyl ether and etc., with preference to ethyl acetate.

In the inert solvent, pyroglutamic acid is used in the amount of 1–2 equivalents and preferably in the amount of 1.02–1.2 equivalents per equivalent of amlodipine. The reaction is performed at −5 to 30° C. and preferably at 25° C. for 0.5 to 5 hours and preferably for 1 to 2 hours.

According to the method of the present invention, amlodipine pyroglutamate can be prepared at a yield of 90% or higher.

Also, the present invention encompasses a pharmaceutical composition useful in the treatment of ischemic cardiac disorders or hypertension, which comprises a therapeutically effective amount of amlodipine pyroglutamate and a pharmaceutically acceptable diluent or carrier.

The composition of the present invention may be formulated into oral dosage forms including, but not limited to, granules, powders, solutions, tablets, capsules, dry syrup and the like, or parenteral dosage forms including injectables. The composition of the present invention is preferably formulated in the dosage form of tablets, capsules, solutions or injectables.

To be therapeutically effective, amlodipine pyroglutamate is administered in the amount of 2–10 mg per day on the basis of the weight of amlodipine. In a unit dosage form, amlodipine pyroglutamate is contained in the amount of 2.6–13.2 mg.

In practical use, amlodipine pyroglutamate can be combined as the active ingredient in admixture with a pharmaceutically acceptable diluent or carrier selected from among excipients, disintegrants, binders and lubricants, and mixtures thereof. The carrier may take a wide variety of forms depending on the form of the preparation desired for administration. In preparing the composition in a solid dosage form such as a tablet or a hard capsule, there may be employed microcrystalline cellulose, lactose, low-substituted hydroxycellulose and the like as an excipient; sodium starch glycollate, anhydrous monohydrogenphosphate and the like as a disintegrant; polyvinylpyrrolidone, low-substituted hydroxypropylcellulose, hydroxypropylcellulose and the like as a binder; and magnesium stearate, silica, talc and the like as a lubricant.

A formulation may comprise an additive to provide sheen to the tablet such as anhydrous dibasic calcium phosphate. To prevent atmospheric moisture from penetrating into the tablet, it may have a water-insoluble coating. The coating base must have a dense molecular structure and preferably, low solubility in water. Suitable for the base is a polymeric material selected from among methacrylic acid copolymer, hydroxypropylmethyl cellulose phthalate, cellulose acetate phthalate, hydroypropylmethylcellulose acetate succinate, polyvinyl alcohol and combinations thereof. Also, the coating may comprise conventional additives such as plasticizers, preservatives, coloring agents, light shielders, etc.

The composition of the present invention may be in the form of solutions such as sterile aqueous solution, or injectables. Preferably such solution contains from 10 to 40% of propylene glycol and sodium chloride sufficient to avoid hemolysis (e.g. about 1%).

A better understanding of the present invention may be obtained in light of the following examples which are set forth to illustrate, but are not to be construed to limit the present invention.

EXAMPLES

Amlodipine pyroglutamate prepared according to the present invention was tested for various physical properties. First, the salt was formulated into tablets, capsules and aqueous solutoins to test processability for dosage formation. Also, amlodipine pyroglutamate was compared with known salts of amlodipine with regard to hydroscopicity, solubility, stability and light stability.

In the following reference examples, conventional salts of amlodipine were prepared according to methods disclosed in the art.

Reference Example 1

Preparation of Amlodipine Besylate

Amlodipine was prepared as disclosed in Korean Pat. Publication No. 87-809. The method described in Korean Pat. Publication No. 95-7228 was adopted to produce amlodipine besylate.

Reference Example 2

Preparation of Amlodipine para-Toluenesulfonate

In 100 ml of methanol was dissolved 20 g of para-toluenesulfonic acid. To the solution, 40 g of the amlodipine prepared in Reference Example 1 in 500 ml of methanol was added dropwise, followed by stirring at 23° C. for 3 hours.

After being filtered off, the solid thus produced was washed with 100 ml of methanol and 100 ml of n-hexane and dried in vacuo.

Reference Example 3

Preparation of Amlodipine Hydrochloride

To 100 ml of methanol was added 12 ml of conc-hydrochloric acid. 54 g of amlodipine prepared in Reference Example 1 in 500 ml of methanol was added dropwise, followed by stirring at 23° C. for 3 hours.

After being filtered off, the solid thus produced was washed with 100 ml of each methanol and 100 ml of n-hexane and dried in vacuo.

Example 1

Preparation of Amlodipine (S)-(−)-Pyroglutamate

Amlodipine (10g, 0.025 mole) was dissolved in ethyl acetate (100 ml) with stirring. The solution was adjusted to 25° C. and slowly added with (S)-(−)-pyroglutamic acid (3.61g, 0.028 mole). This reaction was stirred at 25° C. for 1 hour to produce precipitates. They were filtered off and washed with ethyl acetate (50 ml), followed by drying at 40° C. under vacuum to give 12.82 g of the title compound (Yield 95.3%).

The element analysis and melting point of the amlodipine (S)-(−)-pyroglutamate prepared above were determined.

TABLE 1

| Element analysis for $C_{25}H_{31}N_3O_8Cl$ (%) | | | | |
|---|---|---|---|---|
| Found | C: 55.1 | H: 5.9 | N: 7.9 | O: 22.9 |
| Calculated | C: 55.7 | H: 5.8 | N: 7.8 | O: 23.8 |

Melting point: 183° C. (measured by capillary melting point method with heating rate of about 1° C./minute)

Example 2

Preparation of Amlodipine (R)-(+)-Pyroglutamate

The same procedure as in Example 1 was repeated, with the exception that (R)-(+)-pyroglutamic acid was used instead of (S)-(−)-pyroglutamic acid, to obtain 12.80 g of amlodipine (R)-(+)-pyroglutamic acid (Yield 95.1%).

The element analysis and melting point of the amlodipine (R)-(+)-pyroglutamate prepared above were determined.

TABLE 2

| Element analysis for $C_{25}H_{31}N_3O_8Cl$ (%) | | | | |
|---|---|---|---|---|
| Found | C: 55.2 | H: 5.9 | N: 7.8 | O: 22.8 |
| Calculated | C: 55.7 | H: 5.8 | N: 7.8 | O: 23.8 |

Melting point: 180° C. (measured by capillary melting point method with heating rate of about 1° C./minute)

Example 3

Preparation of Amlodipine Pyroglutamate (Racemate)

The same procedure as in Example 1 was repeated, with the exception that racemic pyroglutamic acid was used instead of (S)-(−)-pyroglutamic acid, to obtain 12.80 g of racemic amlodipine pyroglutamic acid (Yield 95.2%).

The element analysis and melting point of the racemic amlodipine pyroglutamate prepared above were determined.

TABLE 3

| Element analysis for $C_{25}H_{31}N_3O_8Cl$ (%) | | | | |
|---|---|---|---|---|
| Found | C: 55.0 | H: 5.8 | N: 7.9 | O: 22.9 |
| Calculated | C: 55.7 | H: 5.8 | N: 7.8 | O: 23.8 |

Melting point: 183° C. (measured by capillary melting point method with heating rate of about 1° C./minute)

Example 4

Formulation of Tablet Containing Amlodipine Pyroglutamate

The ingredients given in Table 4 were formulated to prepare a tablet containing amlodipine (S)-(−)-pyroglutamate.

TABLE 4

| Ingredients | Contents (mg per tablet) |
|---|---|
| Amlodipine (S)-(−)-PyroGlu | 5.0 based on Amlodipine |
| Low-substituted Hydroxypropylcellulose | 65 |
| Microcrystalline Cellulose | 120 |
| Sodium Starch Glycollate | 4 |
| Magnesium Stearate | 2 |

The ingredients were blended and the blend was compressed using a roller press form Jowoon Machinery, and then the compressed material was formulated into tablets using a tableting machine from Erweka.

Example 5

Formulation of Tablet Containing Amlodipine Pyroglutamate

The ingredients given in Table 5 were formulated to prepare a tablet containing amlodipine (S)-(−)-pyroglutamate.

TABLE 5

| Ingredients | Contents (mg per tablet) |
| --- | --- |
| Amlodipine (S)-(−)-PyroGlu | 5.0 based on Amlodipine |
| Lactose | 180 |
| Cross Povidone | 6 |
| Polyvinylpyrrolidone | 6 |
| Sodium Starch Glycollate | 4 |
| Magnesium Stearate | 2 |

Lactose, cross povidone and polyvinylpyrrolidone K90 were preblended. The pre-blend was granulated according to a fluidized bed assembly method (SPIRA FLOW) and the granules were blended with the remaining ingredients and formulated into tablets using a tableting machine from Erweka.

Example 6
Formulation of Capsule Containing Amlodipine Pyroglutamate

The ingredients given in Table 6 were formulated to prepare a capsule containing amlodipine (S)-(−)-pyroglutamate.

TABLE 6

| Ingredients | Contents (mg per tablet) |
| --- | --- |
| Amlodipine (S)-(−)-PyroGlu | 5.0 based on Amlodipine |
| Low-substituted Hydroxypropylcellulose | 65 |
| Microcrystalline Cellulose | 120 |
| Sodium Starch Glycollate | 4 |
| Magnesium Stearate | 2 |

The ingredients were blended and the blend was compressed using a roller press from Jowoon machinery, and the compressed material was then filled into hard gelatin capsules using a capsule filling device from Bosche.

Example 7
Formulation of Capsule Containing Amlodipine Pyroglutamate

The ingredients given in Table 7 were formulated to prepare a capsule containing amlodipine (S)-(−)-pyroglutamate.

TABLE 7

| Ingredients | Contents (mg per tablet) |
| --- | --- |
| Amlodipine (S)-(−)-PyroGlu | 5.0 based on Amlodipine |
| Lactose | 180 |
| Cross Povidone | 6 |
| Polyvinylpyrrolidone K90 | 6 |
| Sodium Starch Glycollate | 4 |
| Magnesium Stearate | 2 |

Lactose, cross povidone and polyvinylpyrrolidone K90 were preblended. The pre-blend was granulated according to a fluidized bed assembly method (SPIRA FLOW) and the granules were blended with the remaining ingredients and filled in hard gelatin capsules using a capsule filling machine from Bosche.

Example 8
Test for Hygroscopicity of Amlodipine Pyroglutamate

Amlodipine (S)-(−)-pyroglutamate prepared in Example 1 and amlodipine besylate prepared in Reference Example 1 were tested for hygroscopicity by measuring their water contents at 25° C. at different humidity levels. The results are given in Table 8, below.

TABLE 8

| Humidity Conditions (RH) | | 25% | 60% | 75% | 90% |
| --- | --- | --- | --- | --- | --- |
| Storage Period (week) | Initial | 1 | 1 | 1 | 1 |
| (S)-(−)-PyroGlu (%) | 0.3 | 0.26 | 0.3 | 0.31 | 0.32 |
| Besylate (%) | 0.14 | 0.10 | 0.09 | 0.15 | 0.17 |

As shown in Table 8, amlodipine pyroglutamate kept its initial water content without great fluctuation for one week under various humidity conditions, like amlodipine besylate.

Example 9
Test for Solubility of Amlodipine Pyroglutamate

Solubilities of amlodipine (S)-(−)-pyroglutamate prepared in Example 1 and amlodipine besylate prepared in Reference Example 1 in various solvents were measured at 37° C. The results are given in Table 9, below. The solubilities (mg/ml) of Table 6 are values based on the weight of amlodipine converted from the salts.

TABLE 9

| | Salts (mg/ml) | | |
| --- | --- | --- | --- |
| Solvents | PyroGlu | Besylate | Note |
| Dist. Water | 500≦ | 2.00 | Ionic Strength 0.2 buffer |
| pH 3 | 400≦ | 3.25 | Dissolved at 37° C. |
| pH 5 | 400≦ | 3.15 | |
| pH 6 | 400≦ | 3.19 | |
| pH 7 | 200≦ | 1.59 | |
| pH 8 | 200≦ | 1.39 | |

As shown in Table 9, solubilities of amlodipine pyroglutamate in distilled water and buffers of various pH are at least 200 times greater than those of amlodipine besylate. That is, amlodipine pyroglutamate shows far superior solubility properties over amlodipine besylate.

Example 10
Test for Stability of Amlodipine Pyroglutamate

1. Chemical stability of amoldipine pyroglutamate in solid state Amlodipine (S)-(−)-pyroglutamate prepared in Example 1 and amlodipine besylate prepared in Reference Example 1 were subjected to accelerated test at 60° C. and the results are summarized in Table 10, below.

TABLE 10

| | Storage Period | | | |
| --- | --- | --- | --- | --- |
| Salts | initial | 1 week | 2 weeks | 4 weeks |
| PyroGlu | 99.6% | 99.6% | 99.5% | 99.2% |
| Besylate | 99.6% | 99.6% | 99.4% | 99.2% |

1. HPLC Analysis Conditions:

Detector: UV Absorbance (at 237 nm)

Column: Octadesyl silica gel C18 (4.6 mm×150mm, 5 μm)

Mobile Phase: Potassium dihydrogenphosphate monobasic (0.03M): methanol=4:6 (v/v)

Flow Rate: 1.5 m/min

As shown in Table 10, there were virtually no changes in the content of amlodipine pyroglutamate, like amlodipine besylate, as measured by accelerated test at 60° C. The data of Table 10 demonstrate that, comparable to that of amlodipine besylate, the chemical stability of amlodipine pyroglutamate is excellent.

2. Chemical Stability of Amlodipine Pyroglutamate in Aqueous State

To investigate the stability in an aqueous state, amlodipine (S)-(−)-pyroglutamate prepared in Example 1 and amlodipine besylate prepared in Reference Example 1 were separately dissolved in distilled water. The resulting aqueous solutions were stored at 25° C. for 4 weeks in complete darkness, after which a measurement was made of the contents of the salts with resort to HPLC under the same conditions as in the solid state.

The results of the light-shielded stability test indicate that neither decomposition products nor content change is found in both amlodipine pyroglutamate and amlodipine besylate.

Example 1

Test for light Stability of Amlodipine Pyroglutamate

Amlodipine (S)-(−)-pyroglutamate prepared in Example 1, amlodipine besylate, and other salts of amlodipine were separately dissolved in distilled water. The resulting aqueous solutions were stored at 25° C. for 4 weeks while being exposed to daylight. A measurement was made of the contents of the salts with resort to HPLC under the same conditions as in the chemical stability test. The results are given in Table 11, below.

TABLE 11

| Salts | Initial Content (HPLC) | Stored for 4 weeks at 25° C. daylight Content (HPLC) |
|---|---|---|
| (S)-(−)-PyroGlu | 99.5% | 98.5% |
| Besylate | 99.2% | 82.5% |
| Tosylate | 99.2% | 72.0% |
| Hydrochloride | 99.0% | 60.5% |

As shown in Table 11, a smaller reduction in content was found in amlodipine (S)-(−)-pyroglutamate than in the other salts of amlodipine. It was also found that amlodipine besylate turned yellow from white while amlodipine (S)-(−)-pyroglutamate showed no color change. These data accordingly show that amlodipine (S)-(−)-pyroglutamate is superior in light stability to amlodipine besylate.

Taken together, the data presented in the above examples indicate that the amlodipine pyroglutamate of the present invention has excellent physicochemical properties including non-hygroscopicity, chemical and light stability, solubility and processability for dosage formulation and is easy to deliver in the body of a patient in addition to being stored for a long period of time. Further, free of both corrosiveness and toxicity, pyroglutamic acid is industrially useful.

What is claimed is:

1. A pyroglutamic acid salt of amlodipine.
2. The pyroglutamic acid salt of amlodipine as defined in claim 1, wherein the pyroglutamic acid is (S)-(−)-pyroglutamic acid or (R)-(+)-pyroglutamic acid.
3. The pyroglutamic acid salt of amlodipine as defined in claim 1, wherein the salt is in crystalline form.
4. The pyroglutamic acid salt of amlodipine as defined in claim 1, wherein the salt is light-stable.

* * * * *